(12) United States Patent
Ourada

(10) Patent No.: US 8,900,232 B2
(45) Date of Patent: Dec. 2, 2014

(54) BIFURCATED SHAFT FOR SURGICAL INSTRUMENT

(75) Inventor: Paul E. Ourada, Longmont, CO (US)

(73) Assignee: Covidien LP, Mansfield, MA (US)

( * ) Notice: Subject to any disclaimer, the term of this patent is extended or adjusted under 35 U.S.C. 154(b) by 858 days.

(21) Appl. No.: 13/102,604

(22) Filed: May 6, 2011

(65) Prior Publication Data

US 2012/0283734 A1 Nov. 8, 2012

(51) Int. Cl.
*A61B 18/14* (2006.01)
*A61B 18/00* (2006.01)
*A61B 17/29* (2006.01)

(52) U.S. Cl.
CPC ..... *A61B 18/1445* (2013.01); *A61B 2018/0063* (2013.01); *A61B 2017/2936* (2013.01); *A61B 2017/2937* (2013.01); *A61B 2017/2944* (2013.01)
USPC .......................................................... 606/51

(58) Field of Classification Search
CPC .. A61B 17/28; A61B 17/282; A61B 18/1445; A61B 18/1447; A61B 2017/2926; A61B 2017/2933; A61B 2018/00404; A61B 2018/0063; A61B 2018/145
USPC .......................... 606/41, 45, 51, 52, 205–207
See application file for complete search history.

(56) References Cited

U.S. PATENT DOCUMENTS

| D249,549 | S | | 9/1978 | Pike |
| D263,020 | S | | 2/1982 | Rau, III |
| 4,485,811 | A | | 12/1984 | Chernousov et al. |
| D295,893 | S | | 5/1988 | Sharkany et al. |
| D295,894 | S | | 5/1988 | Sharkany et al. |
| D298,353 | S | | 11/1988 | Manno |
| D299,413 | S | | 1/1989 | DeCarolis |
| D343,453 | S | | 1/1994 | Noda |
| 5,318,589 | A | * | 6/1994 | Lichtman ...................... 606/205 |
| D348,930 | S | | 7/1994 | Olson |

(Continued)

FOREIGN PATENT DOCUMENTS

| DE | 2415263 | 10/1975 |
| DE | 2514501 | 10/1976 |

(Continued)

OTHER PUBLICATIONS

U.S. Appl. No. 08/926,869, filed Sep. 10, 1997, James G. Chandler.

(Continued)

*Primary Examiner* — Michael Peffley
*Assistant Examiner* — Daniel Fowler

(57) ABSTRACT

A surgical instrument includes a shaft having a proximal end and a bifurcated distal end defining a first shaft portion and a second shaft portion. An end effector assembly is disposed at the distal end of the shaft and includes first and second jaw members. One (or both) of the jaw members is moveable relative to the other between an open position and a closed position for grasping tissue therebetween. Each of the jaw members defines an opposed jaw surface and is independently coupled to one of the first and second shaft portions. The first and second shaft portions are configured to flex relative to one another during movement of the jaw members to the closed position to grasp tissue therebetween such that the opposed jaw surfaces of the jaw members are disposed in substantially parallel orientation relative to one another when grasping tissue therebetween.

16 Claims, 4 Drawing Sheets

(56) References Cited

U.S. PATENT DOCUMENTS

| | | | |
|---|---|---|---|
| D349,341 S | 8/1994 | Lichtman et al. | |
| 5,334,198 A * | 8/1994 | Hart et al. | 606/52 |
| D354,564 S | 1/1995 | Medema | |
| D358,887 S | 5/1995 | Feinberg | |
| D384,413 S | 9/1997 | Zlock et al. | |
| 5,797,958 A * | 8/1998 | Yoon | 606/207 |
| D402,028 S | 12/1998 | Grimm et al. | |
| D416,089 S | 11/1999 | Barton et al. | |
| 6,030,384 A * | 2/2000 | Nezhat | 606/48 |
| D424,694 S | 5/2000 | Tetzlaff et al. | |
| D425,201 S | 5/2000 | Tetzlaff et al. | |
| 6,096,037 A * | 8/2000 | Mulier et al. | 606/49 |
| 6,102,909 A | 8/2000 | Chen et al. | |
| 6,270,508 B1 | 8/2001 | Klieman et al. | |
| D449,886 S | 10/2001 | Tetzlaff et al. | |
| D454,951 S | 3/2002 | Bon | |
| D457,958 S | 5/2002 | Dycus et al. | |
| D457,959 S | 5/2002 | Tetzlaff et al. | |
| 6,464,703 B2 * | 10/2002 | Bartel | 606/51 |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| 7,195,631 B2 | 3/2007 | Dumbauld | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,566,334 B2 * | 7/2009 | Christian et al. | 606/51 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2001/0031975 A1 | 10/2001 | Whitman et al. | |
| 2003/0114851 A1 | 6/2003 | Truckai et al. | |
| 2005/0137590 A1 * | 6/2005 | Lawes et al. | 606/45 |
| 2006/0190035 A1 | 8/2006 | Hushka et al. | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 02617 | 12/2005 |
| DE | 20 2007 00916 | 10/2007 |
| DE | 20 2007 00931 | 10/2007 |
| DE | 19738457 | 1/2009 |
| DE | 10 2008 01840 | 7/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 6-285078 | 10/1994 |
| JP | 6-511401 | 12/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| SU | 401367 | 11/1974 |
| WO | WO 00/36986 | 6/2000 |
| WO | WO 00/72765 | 12/2000 |
| WO | WO 01/03587 | 1/2001 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 20, 2000, Thomas P. Ryan.
U.S. Appl. No. 12/336,970, filed Dec. 17, 2008, Paul R. Sremcich.
U.S. Appl. No. 12/576,380, filed Oct. 9, 2009, Wayne Siebrecht.
U.S. Appl. No. 12/607,191, filed Oct. 28, 2009, William H. Nau, Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.

(56) References Cited

OTHER PUBLICATIONS

U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. "12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, Dec. 30, 2010, John R. Twomey.
U.S. Appl. No. 13/004,984, filed Jan. 12, 2011, David M. Garrison.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.

(56) References Cited

OTHER PUBLICATIONS

E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended- EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
EP Search Report EP 10 01 2644 dated Mar. 3, 2011.

* cited by examiner

BIFURCATED SHAFT FOR SURGICAL INSTRUMENT

BACKGROUND

1. Technical Field

The present disclosure relates to surgical instruments and, more particularly, to bifurcated shafts for use with surgical instruments.

2. Description of Related Art

Electrosurgical instruments (e.g., surgical forceps) are well known in the medical field, and typically include a handle, a shaft, and an end effector assembly that is operatively coupled to a distal portion of the shaft to manipulate tissue (e.g., grasp and seal tissue). Electrosurgical instruments utilize both mechanical clamping action and electrical energy to effect hemostasis by heating the tissue and blood vessels to coagulate, cauterize, seal, cut, desiccate, and/or fulgurate tissue.

As an alternative to open electrosurgical instruments for use with open surgical procedures, many modern surgeons use endoscopes and endoscopic electro surgical instruments (e.g., endoscopic forceps) for remotely accessing organs through smaller, puncture-like incisions. As a direct result thereof, patients tend to benefit from less scarring, fewer infections, shorter hospital stays, less pain, less restriction of activity, and reduced healing time. Typically, the endoscopic electrosurgical instrument is inserted into the patient through one or more various types of cannulas or access ports (typically having an opening that ranges from about five millimeters to about twelve millimeters) that has been made with a trocar.

Conventional electrosurgical instruments include a pair of jaw members that have a common pivot point (e.g., a pivot pin) disposed towards proximal ends thereof that facilitates manipulation of the jaw members between open and closed positions. In addition, the pivot point facilitates application of pressure by the jaw members to tissue grasped therebetween by preventing the opposed jaw surfaces from moving away from each other at the proximal ends of the jaw members. In this manner, when tissue is grasped between the opposing jaw members, a V-shaped configuration is defined therebetween since the distal ends of the jaw members are further away from each other than the proximal ends of the jaw members. When smaller-diametered tissue is grasped between the jaw members, the V-shaped configuration does not create any substantial problems, since the opposing jaw members are substantially parallel and relatively close to each other. However, when larger-diametered tissue is grasped between the jaw members, the opposing jaw surfaces are not substantially parallel to each other and further away from each other, thus inhibiting complete closure of the jaw members. More particularly, when larger-diametered tissue is grasped between the jaw members, the current density applied to tissue grasped therebetween during surgical treatment (e.g., fusion or ablation) tends to be substantially higher at the proximal end of the jaw members than towards the distal portion thereof, which creates uneven tissue fusion, or uneven ablation.

SUMMARY

In accordance with one embodiment of the present disclosure, a surgical instrument is provided. The surgical instrument includes a shaft having a proximal end and a bifurcated distal end defining a first shaft portion and a second shaft portion. An end effector assembly is disposed at the distal end of the shaft and includes first and second jaw members. One or both of the jaw members is moveable relative to the other between an open position and a closed position for grasping tissue therebetween. Each of the jaw members defines an opposed jaw surface. Further, each of the jaw members is independently coupled to one of the first and second shaft portions. The first and second shaft portions are configured to flex relative to one another during movement of the jaw members to the closed position to grasp tissue therebetween such that the opposed jaw surfaces of the jaw members are disposed in substantially parallel orientation relative to one another when grasping tissue therebetween.

In one embodiment, the opposed jaw surfaces define electrically conductive tissue sealing surfaces adapted to connect to a source of energy for sealing tissue grasped therebetween.

In another embodiment, the first and second shaft portions are configured to flex relative to one another to achieve a uniform closure pressure between the jaw members when grasping tissue therebetween. The closure pressure may be in the range of about 3 kg/cm$^2$ to about 16 kg/cm$^2$ during tissue sealing.

In still another embodiment, the first and second shaft portions are configured to flex relative to one another to achieve a uniform gap distance between the jaw members during tissue sealing.

In yet another embodiment, the shaft is bifurcated about a vertical axis thereof to define a first side shaft portion and a second side shaft portion. Alternatively, the shaft may be bifurcated about a horizontal axis thereof to define an upper shaft portion and a lower shaft portion.

In still yet another embodiment, each of the jaw members is independently coupled to one of the first and second shaft portions via a floating pivot.

In another embodiment, a cowling disposed about a portion of the bifurcated shaft and/or the jaw members. The cowling is configured to limit flexing of the first and second shaft portions relative to one another and/or may be disposed within a recess, or notch to retain the cowling in position about the bifurcated shaft and/or jaw members.

A surgical instrument provided in accordance with another embodiment of the present disclosure includes a shaft having a proximal end and a bifurcated distal end defining a first shaft portion and a second shaft portion. An end effector assembly is disposed at the distal end of the shaft and includes first and second jaw members, each defining an opposed jaw surface. The first jaw member is coupled to the first shaft portion via a first floating pivot and the second jaw member is coupled to the second shaft portion via a second floating pivot independent of the first floating pivot. The first and second jaw members are rotatable about the first and second floating pivots, respectively, relative to one another between an open position and a closed position for grasping tissue therebetween. The first and second floating pivots are moveable relative to one another as the jaw members are rotated to the closed position for grasping tissue therebetween such that the opposed jaw surfaces of the jaw members are disposed in substantially parallel orientation relative to one another when grasping tissue therebetween.

In one embodiment, the opposed jaw surfaces define electrically conductive tissue sealing surfaces adapted to connect to a source of energy for sealing tissue grasped therebetween.

In another embodiment, the first and second floating pivots are moveable relative to one another to achieve a uniform closure pressure between the jaw members during tissue sealing, e.g., between about 3 kg/cm$^2$ to about 16 kg/cm$^2$.

In another embodiment, the first and second floating pivots are moveable relative to one another to achieve a uniform gap distance between the jaw members during tissue sealing.

In still another embodiment, the shaft is bifurcated about a vertical axis thereof to define a first side shaft portion and a second side shaft portion. Alternatively, the shaft may be bifurcated about a horizontal axis thereof to define an upper shaft portion and a lower shaft portion.

In yet another embodiment, the first and second shaft portions are configured to flex relative to one another to permit movement of the first and second floating pivots relative to one another.

In still yet another embodiment, a cowling is disposed about a portion of the bifurcated shaft and/or the jaw members to limit movement of the first and second floating pivots relative to one another. Further, the cowling may be disposed within a recess, or notch to retain the cowling in position about the bifurcated shaft and/or jaw members.

BRIEF DESCRIPTION OF THE DRAWINGS

Various embodiment of the subject instrument are described herein with reference to the drawings wherein.

DETAILED DESCRIPTION

Figure 1A:
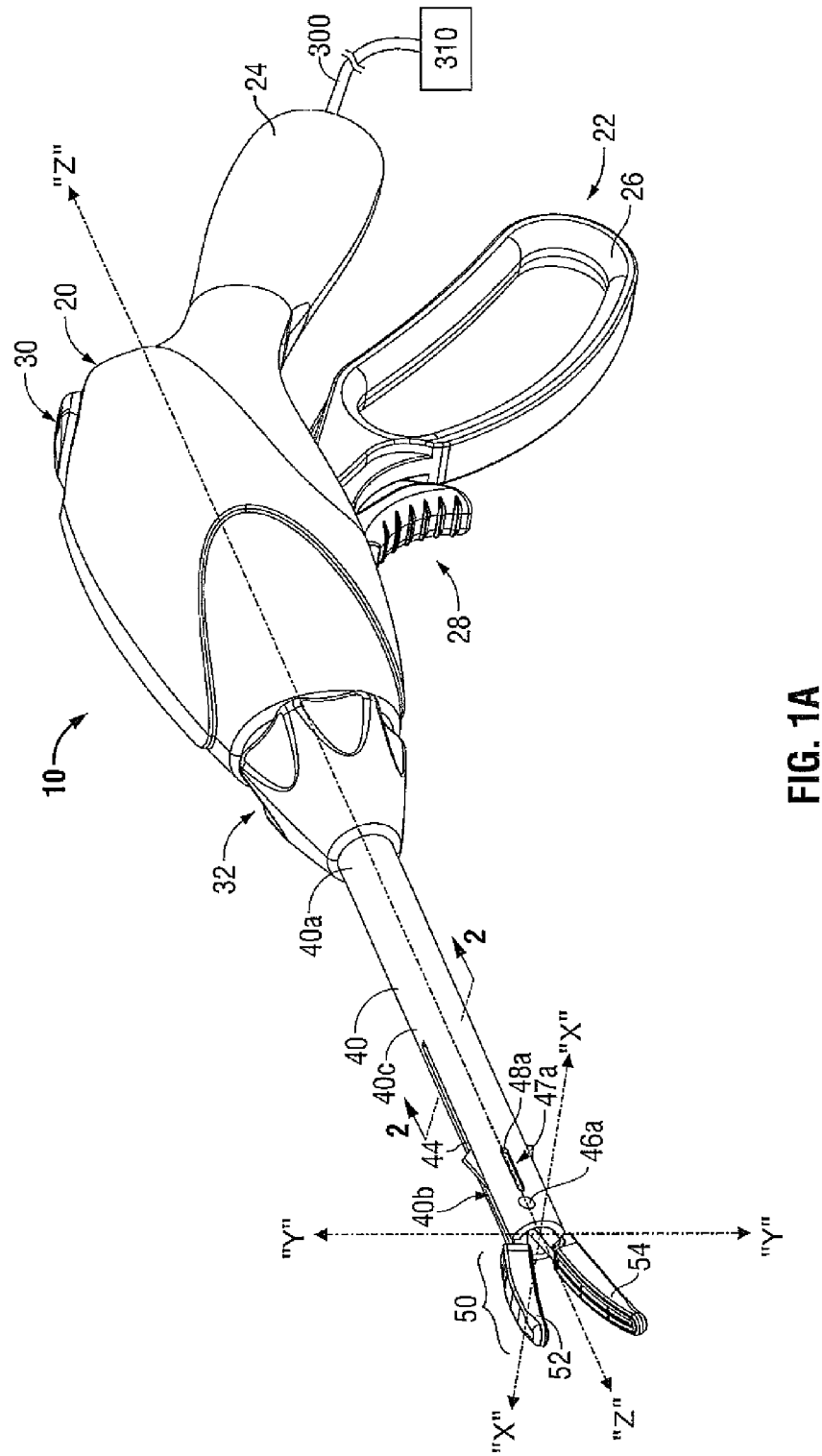
FIG. 1A is a front, perspective view of a surgical instrument in accordance with an embodiment of the present disclosure including a vertically bifurcated shaft.

Embodiments of the presently-disclosed surgical instrument are described in detail with reference to the drawings wherein like reference numerals identify similar or identical elements. As used herein, the term "distal" refers to that portion of the instrument that is that is further from a user, while the term "proximal" refers to that portion of the instrument that is closer to a user.

In accordance with the present disclosure, an electrosurgical instrument is provided to include an end effector assembly having two opposing jaw members that are independently coupled to a shaft having a bifurcated configuration at a distal portion thereof. The bifurcated shaft includes two flexible half shafts that are configured to bend or flex away from each other when pressure is exerted therebetween. Each of the jaw members are pivotally coupled to the respective flexible half shaft at a respective floating pivot point such that each jaw member may independently move away from the other when grasping and sealing tissue therebetween. In this configuration, the flexible half shafts flex or bend away from each other to allow the jaw members to pivot towards a parallel configuration instead of a V-shaped configuration. A more detailed explanation of the novel bifurcated shaft having floating pivot points and various embodiments thereof is discussed in greater detail below.

Turning now to FIG. 1A, an embodiment of a surgical instrument 10 is shown for use with various surgical procedures and generally includes a housing 20, a handle assembly 22, a trigger assembly 28, a switch 30, a rotating assembly 32, and an end effector assembly 50 having jaw members 52 and 54 that mutually cooperate to grasp, seal, and divide tubular vessels and vascular tissue.

Surgical instrument 10 also includes a shaft 40 that has a proximal portion 40a and a vertically bifurcated distal portion 40b that mechanically engages end effector assembly 50, as will be described in greater detail below. As schematically depicted in FIG. 1A, a longitudinal axis "Z-Z" is defined along shaft 40, a horizontal axis "X-X" axis is defined in a transverse relation to longitudinal axis "Z-Z," and a vertical axis "Y-Y" is defined in a perpendicular relation to both longitudinal axis "Z-Z" and horizontal axis "X-X."

In some embodiments, electrosurgical instrument 10 may include an electrosurgical cable 300 that connects electrosurgical instrument 10 to a source of electrosurgical energy 310 (e.g., a generator). Cable 300 is internally divided into several cable leads (not explicitly shown) such that each transmits electrical potentials through their respective feed paths through electrosurgical instrument 10 to end effector assembly 50. In other embodiments, electrosurgical instrument 10 may include an internal source of electrosurgical energy (not shown) that is disposed within housing 20, for example, but not limited to a battery. In some embodiments, electrosurgical energy may be transmitted to sealing surfaces 56, 58 (FIG. 3) of jaw members 52, 54, respectively, by switch 30 to treat tissue grasped therebetween. Switch 30 is disposed on housing 20 such that when jaw members 52 and 54 are in the closed configuration, a user may initiate the delivery of electrosurgical energy to jaw members 52 and 54 by conveniently manipulating switch 30.

Still referring to FIG. 1A, handle assembly 22 includes a fixed handle 24 and a movable handle 26 that are configured to be manipulated by a user. Fixed handle 24 is integrally associated with housing 20 and handle 26 is movable relative to fixed handle 24 as explained in greater detail below with respect to the operation of surgical instrument 10. Rotating assembly 32 is operatively connected to the housing 20 and is rotatable in either direction about longitudinal axis "Z-Z" to similarly rotate end effector assembly 50 about longitudinal axis "Z-Z." More particularly, when rotating assembly 32 is rotated by a user in a clockwise or a counterclockwise direction, shaft 40 is similarly rotated which, in turn, rotates end effector assembly 50 in the respective clockwise or counterclockwise direction.

For a more detailed description of handle assembly 22, rotating assembly 32, and electrosurgical cable 300 (including line-feed configurations and/or connections) reference is made to commonly-owned U.S. Pat. No. 7,766,910 to Hixson et al. and U.S. Pat. No. 7,255,697 to Dycus et al.

Figure 2:
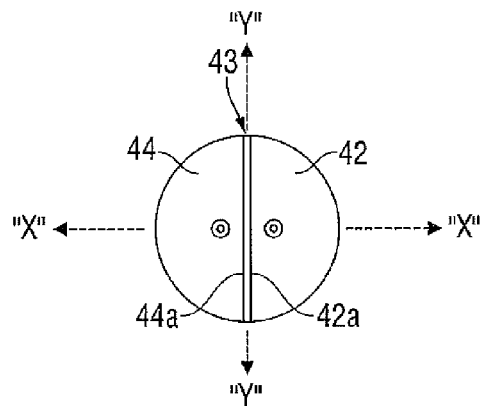
FIG. 2 is a front, cross-sectional view of the vertically bifurcated shaft of FIG. 1A taken along section line 2-2.

As best shown in FIG. 2, in conjunction with FIG. 1A, shaft 40 includes proximal portion 40a and bifurcated distal portion 40b. Proximal portion 40a of shaft 40 mechanically engages a distal portion of housing 20 and is received within housing 20 such that appropriate mechanical and electrical connections relating thereto are established. Vertically bifurcated distal portion 40b of shaft 40 has a split-shaft configuration that includes a first half shaft 42 and a second half shaft 44. First half shaft 42 and second half shaft 44 each include a respective vertical planar surface 42a and 44a that are substantially parallel to each other and along vertical axis "Y-Y." Vertical planar surfaces 42a and 44a are separated from each other to define a space 43 therebetween.

First half shaft 42 and second half shaft 44 are joined together at a mid-portion 40c (FIG. 1A) of shaft 40. In some embodiments, shaft 40 includes a one-piece configuration from mid-portion 40c to proximal portion 40a. First half shaft 42 and second half shaft 44 are monolithically formed onto shaft 40, or, alternatively, each of first half shaft 42 and second half shaft 44 may be separately attached at mid-portion 40c of shaft 40. In some embodiments, first half shaft 42 and second half shaft 44 have resilient or biasing characteristics to withstand and react to pressure exerted by jaw members 52 and 54 when grasping tissue therebetween and/or during tissue sealing, as will be described in greater detail below with respect to the operation of electrosurgical instrument 10.

Figure 3:
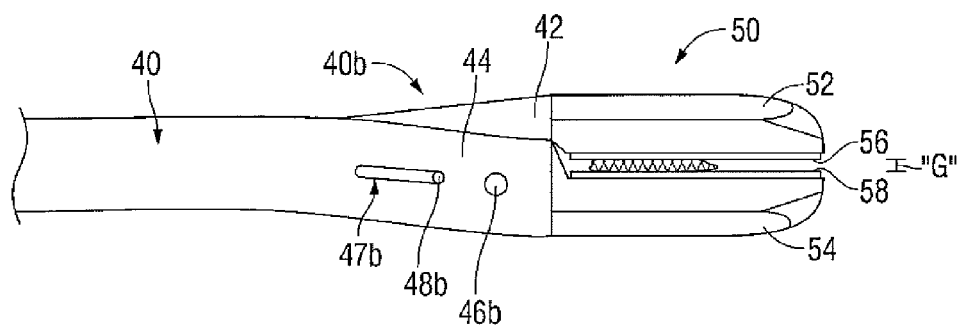
FIG. 3 is an enlarged, side, elevational view of the vertically bifurcated shaft of FIG. 1A.

Referring now to FIGS. 1A and 3, end effector assembly 50 is pivotally attached to vertically bifurcated distal portion 40b of shaft 40. As discussed above, end effector assembly 50 includes a pair of jaw members 52 and 54 that are configured to pivot relative to each other. Movable handle 26 is operatively connected to shaft 40 that mechanically cooperates to impart movement of the jaw members 52 and 54 from an open position (FIG. 1A) wherein the jaw members 52 and 54 are disposed in spaced relation relative to each other, to a clamping or closed position (FIG. 3) wherein the jaw members 52 and 54 cooperate to grasp tissue therebetween.

Each jaw member 52, 54 is independently coupled to distal portion 40b of shaft 40. More particularly, jaw member 52 is pivotally coupled to first half shaft 42 by a pivot pin 46a (e.g., at a pivot point) and jaw member 54 is pivotally coupled to second half shaft 44 by a pivot pin 46b (e.g., at a pivot point). Alternatively, jaw member 52 may be pivotally coupled to second half shaft 44 by a pivot pin 46b and jaw member 54 may be pivotally coupled to first half shaft 42 by a pivot pin 46a. Pivot pins 46a and 46b have a floating pin configuration. In this floating pin configuration, each jaw member 52, 54 is pivotally coupled to respective flexible half shaft 42, 44 by a respective floating pivot pin 46a, 46b such that each jaw member 52, 54 may independently move away from the other, along vertical axis "Y-Y" (see FIGS. 1A and 2) when tissue is grasped therebetween. In this manner, each flexible half shaft, namely first half shaft 42 and second half shaft 44, flexes and/or bends to allow the respective jaw member 52, 54 to pivot via the respective floating pivot pin 46a, 46b towards a parallel configuration, thus preventing the jaws from maintaining the V-configuration during the grasping and sealing of tissue therebetween. With this purpose in mind, first half shaft 42 and second half shaft 44 may be configured to maintain a predetermined pressure exerted by jaw members 52 and 54 during a sealing procedure.

Additionally or alternatively, first half shaft 42 and second half shaft 44 may be configured to apply and/or exert a predetermined threshold pressure towards jaw members 52 and 54. In any of these scenarios, jaw members 52 and 54 are configured to pivot to a closed and substantially parallel configuration, in combination with the first half shaft 42 and second half shaft 44, while maintaining the predetermined threshold pressure to properly effectuate a tissue seal.

In one embodiment, the combination of the mechanical advantage of the floating pin configuration along with the compressive force associated with vertically bifurcated distal portion 40b of shaft 40 facilitates and assures consistent, uniform and accurate closure pressure about the tissue within the desired working pressure range (e.g., sealing threshold pressure) of about 3 kg/cm$^2$ to about 16 kg/cm$^2$ and, more specifically, about 7 kg/cm$^2$ to about 13 kg/cm$^2$. By controlling the intensity, frequency and duration of the electrosurgical energy applied to the tissue, the user can effectively treat tissue (e.g., seal tissue).

In this manner, two mechanical factors play an important role in determining the resulting thickness of the sealed tissue and effectiveness of the seal, i.e., the pressure applied between opposing jaw members 52 and 54 and the gap distance "G" between opposing sealing surfaces 56 and 58 of jaw members 52 and 54 during the sealing process. However, the thickness of the resulting tissue seal cannot be adequately controlled by force alone. In other words, if too much force is exerted, jaw members 52 and 54 may touch and possibly create a short resulting in little energy traveling through the tissue, and thus resulting in a bad tissue seal. If too little force is exerted and the seal would be too thick.

Applying the correct force is important to oppose the walls of the vessel and to reduce the tissue impedance to a low enough value that allows enough current through the tissue. In other scenarios, the correct force is important to overcome the forces of expansion during tissue heating, to ensure adequate force is applied as tissue is "cooked down," or contracted during the sealing process, in addition to contributing towards creating the required end tissue thickness, which is an indication of a proper seal. As such, the tissue impedance may be monitored during sealing to help ensure that an adequate tissue seal is formed.

In some embodiments, at least one jaw member, e.g., 54, may include one or more stop members (not explicitly shown) that limits the movement of the two opposing jaw members 52 and 54 relative to one another. The stop members (not explicitly shown) may extend from the sealing surface 56, 58 of either of both of jaw members 52, 54, respectively, at a predetermined distance according to the specific material properties (e.g., compressive strength, thermal expansion, etc.) to define a minimum gap distance between jaw members 52, 54 during tissue sealing. It is envisioned that the minimum gap distance between opposing sealing surfaces 56 and 58 of jaw members 52, 54 during sealing ranges from about 0.001 inches to about 0.006 inches and, more specifically, between about 0.002 and about 0.005 inches, to inhibit shorting between the sealing surface 56, 58 as tissue is "cooked down," or contracted during the sealing process.

In some embodiments, as best shown in FIGS. 1A and 3, each jaw member 52, 54 may include a cam slot (not explicitly shown) that corresponds to a respective cam slot 47a, 47b defined on each of first half shaft 42 and second half shaft 44. To facilitate movement of jaw members 52 and 54, driving pins 48a and 48b are mechanically coupled to jaw members 52 and 54, respectively, to allow opening and closing of jaw members 52 and 54. Driving pins 48a and 48b independently float with respect to each other and are mechanically coupled to handle assembly 22 (e.g., handle 26) via a respective driving mechanism (not explicitly shown) to facilitate opening and closing of jaw members 52 and 54. More specifically, upon depression of moveable handle 26, the driving mechanism (not explicitly shown) urges drive pins 48a, 48b distally along slots 47a, 47b, respectively, to move jaw members 52, 54 towards the closed position, as shown in FIG. 3. On the other hand, when handle 26 is released, or moved back to its initial position, the driving mechanism (not explicitly shown) pulls drive pins 48a, 48b proximally along slots 47a, 47b, respectively, such that jaw members 52, 54 are returned toward the open position.

As discussed above, jaw members 52 and 54 of end effector assembly 50 are pivotally coupled to respective first and second half shafts 42 and 44, and are remotely operable by handle assembly 22 to open and close jaw members 52 and 54. In particular, end effector assembly 50 may be configured as a bilateral assembly, e.g., where both jaw members 52 and 54 are moveable relative to one another, as shown in FIGS. 1A and 3, or may alternatively be configured as a unilateral assembly, e.g., where only one of jaw members 52, 54 is moveable relative to the other, stationary jaw member 52, 54.

During movement of jaw members 52 and 54 from the open position to the closed position, jaw members 52 and 54 pivot toward each other and bifurcated shafts 42, 44 may flex to allow pivot points 46a, 46b of jaw members 52, 54, respectively, to move away from each other. In this configuration, jaw members 52 and 54 can orient themselves in a substantially parallel configuration such that sealing surfaces 56, 58 are substantially parallel to one another along the lengths thereof. This allows jaw members 52, 54 to rotate about pivot pins 46a and 46b, while at the same time aligning themselves in parallel fashion. As discussed above, the floating pivot pin configuration allows pivot pins 46a, 46b to move away from each other to allow the jaw members to be parallel to each other. In this configuration, a threshold pressure and desired gap distance "G" between sealing surfaces 56, 58 is readily achievable during tissue sealing, even if the size of tissue is altered during application of energy thereto, e.g., as a result of tissue contraction, or "cook-down." Thus, by maintaining an accurate and consistent pressure and gap distance "G," during application of electrosurgical energy to sealing surfaces 56, 58, throughout the sealing process, an effective tissue seal may be formed.

As discussed above, when jaw members 52 and 54 are approximated to the closed configuration and a threshold pressure is reached, first and second half shafts 42 and 44 are configured to "break" or discontinue application of closure pressure. In other words, the flexing, or bending of the shaft halves 42, 44 limits the pressure applied to tissue grasped between jaw members 52, 54 to a threshold pressure and ensures that the jaw members 52 and 54 are closed about tissue in a substantially parallel orientation relative to one another, thus ensuring a consistent and accurate gap "G" therebetween throughout the tissue sealing process. On the other hand, if tissue is contracted during the tissue sealing process, shaft halves 42, 44 are flexed, or bent back to ensure that the desired closure pressure is maintained, i.e., such that the closure pressure does not fall too low.

Figure 1B:
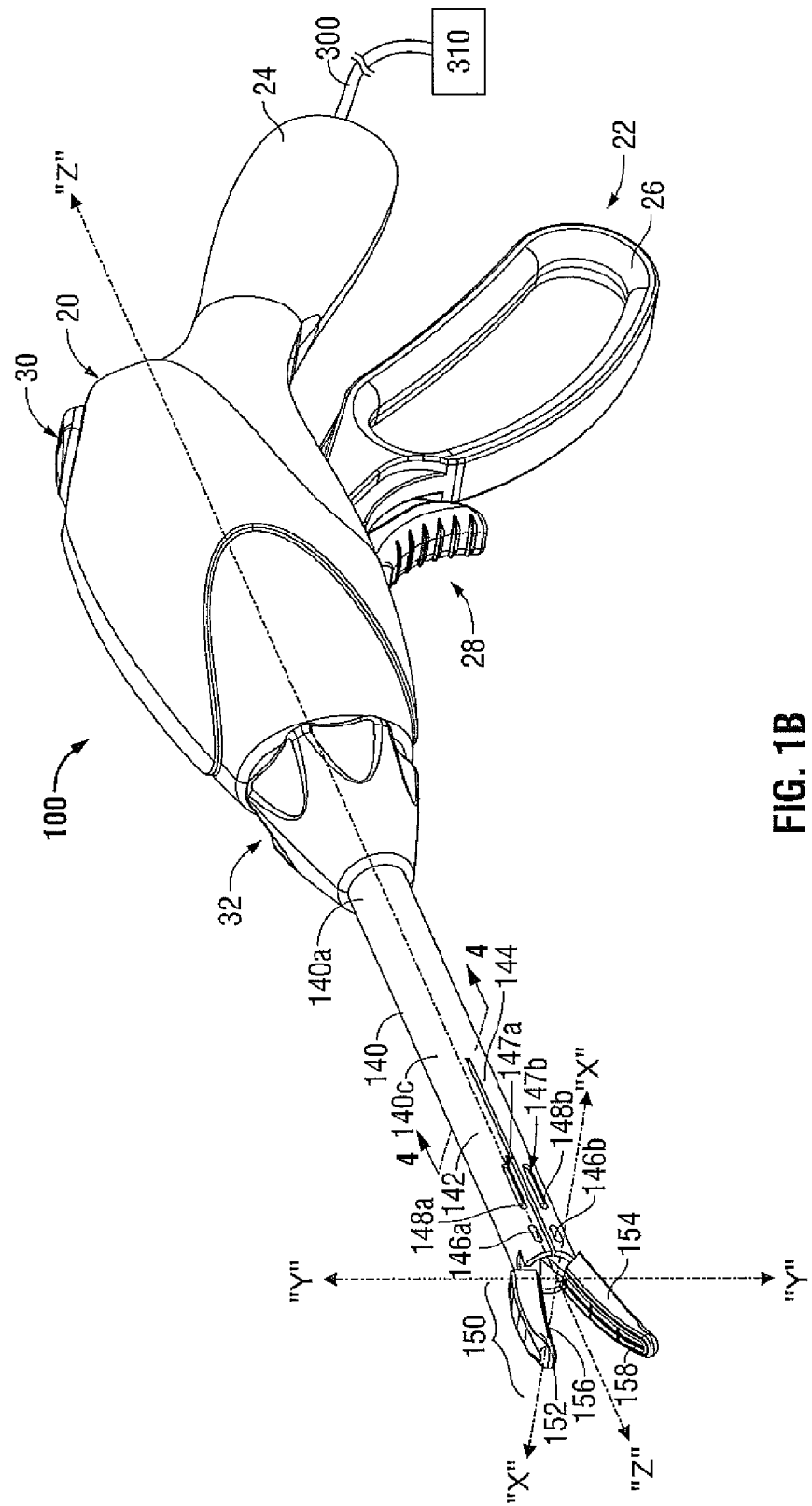
FIG. 1B is a front, perspective view of a surgical instrument in accordance with another embodiment of the present disclosure including a horizontally bifurcated shaft.
Figure 4:
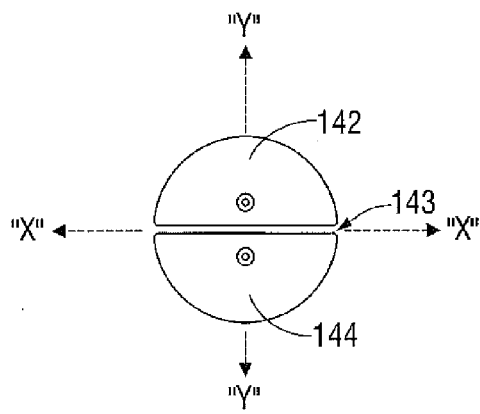
FIG. 4 is a front, cross-sectional view of the horizontally bifurcated shaft of FIG. 1B taken along section line 4-4.
Figure 5:
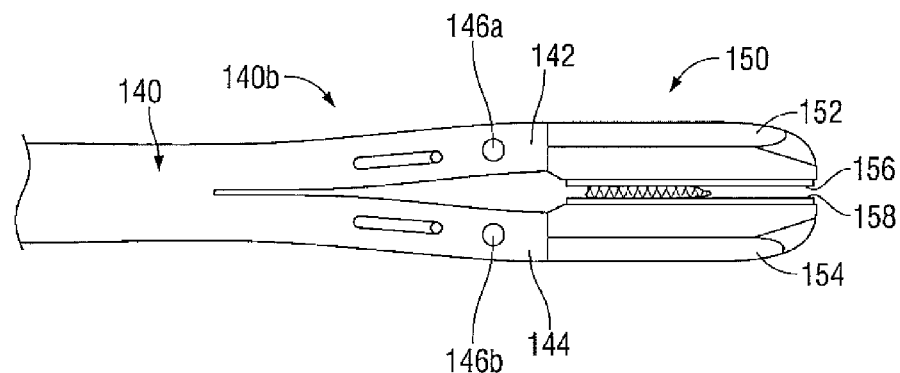
FIG. 5 is an enlarged, side, elevational view of the horizontally bifurcated shaft of FIG. 1B.

Turning now to FIGS. 1B and 4-5, another embodiment of a surgical instrument 100 similar to surgical instrument 10, is described. Surgical instrument 100 is similar to surgical instrument 10 described above with reference to FIGS. 1A and 2-3 and, thus, will only be described generally, while focusing on the differences between surgical instrument 100 and surgical instrument 10.

As shown in FIGS. 1B and 4-5, end effector assembly 150 includes a pair of opposing jaw members 152 and 154 each having an electrically conductive tissue sealing surface 156 and 158, respectively. Jaw members 152 and 154 cooperate with each other to grasp tissue therebetween, as substantially described above with respect to the embodiment of FIGS. 1A-3.

Surgical instrument 100 further includes a shaft 140 having a proximal portion 140a, a mid-portion 140c, and a bifurcated distal portion 140b. Proximal portion 140a of shaft 140 mechanically engages a distal portion of housing 20 and is received within housing 20 such that appropriate mechanical and electrical connections relating thereto are established. Bifurcated distal portion 140b of shaft 140 is similar to bifurcated distal portion 40b of shaft 40 (FIGS. 1A and 3), except that bifurcated distal portion 140b of shaft 140 is split along a horizontal plane relative to horizontal axis "X-X" (rather than the vertically-bifurcated split of shaft 40).

Horizontally bifurcated distal portion 140b of shaft 140 has a split-shaft configuration that includes a first half shaft 142 and a second half shaft 144. First half shaft 142 and second half shaft 144 are separated from each other to define a space 143 therebetween, as best shown in FIG. 4. First half shaft 142 and second half shaft 144 are joined together at mid-portion 140c of shaft 140. In some embodiments, shaft 140 includes a one-piece configuration from mid-portion 140c to proximal portion 140a. First half shaft 142 and second half shaft 144 are monolithically formed onto shaft 140, or, in the alternative, each of first half shaft 142 and second half shaft 144 may be separately attached at mid-portion 140c of shaft 140. In some embodiments, first half shaft 142 and second half shaft 144 have resilient or biasing characteristics to withstand and react to pressure exerted by jaw members 152 and 154 when grasping and sealing tissue therebetween, as will be described in greater detail below with respect to the operation of surgical instrument 100.

Referring now to FIGS. 1B and 5, end effector assembly 150 is pivotally attached to horizontally bifurcated distal portion 140h of shaft 140. As discussed above, end effector assembly 150 includes a pair of jaw members 152 and 154 that are configured to pivot relative to each other. Movable handle 26 is operatively connected to shaft 140 to impart movement of the jaw members 152 and 154 from an open position (FIG. 1B) wherein the jaw members 152 and 154 are disposed in spaced relation relative to each other, to a clamping or closed position (FIG. 5) wherein the jaw members 152 and 154 cooperate with each other to grasp tissue therebetween for sealing and other types of surgical treatments.

Each jaw member 152, 154 is independently coupled to distal portion 140b of shaft 140. More particularly, jaw member 152 is pivotally coupled to first half shaft 142 by a floating pivot pin 146a and jaw member 154 is pivotally coupled to second half shaft 144 by a floating pivot pin 146b. Floating pivot pins 146a, 146b permit jaw member 152, 154 to independently move away from one another along horizontal axis "X-X" when tissue is grasped therebetween. In this manner, each flexible half shaft 142, 144 flexes to allow the respective jaw member 152, 154 to pivot via the respective floating pivot pin 146a, 146b towards a parallel configuration instead of maintaining the known V-configuration when grasping and sealing tissue therebetween FIG. 5 shows surgical instrument 100 grasping tissue between jaw members 152, 154. Once jaws members 152 and 154 are fully compressed about tissue, electrosurgical energy may be supplied to sealing surfaces 156, 158 to seal tissue. The factors, parameters and additional features discussed above with respect to end effector assembly 50 (FIGS. 1A and 3) for adequately sealing tissue apply similarly to end effector assembly 150 and, thus, will not be repeated.

Referring generally to FIGS. 1A and 1B, in some embodiments, a suitable mechanical mechanism may be provided within bifurcated shafts 40, 140, to keep the bifurcated shaft halves 42, 44 and 142, 144, respectively, in an initial position, e.g., wherein shaft halves 42, 44 or 142, 144 are substantially un-flexed or un-bent, for traditional operation of shafts 40, 140 and end effector assemblies 50, 150, respectively, until a sufficient opposition force is present to flex, or bend the shafts halves 42, 44 and 142, 144, respectively, to ensure substantially parallel closure of jaw members 52, 54 and 152, 154, respectively.

Figure 6:
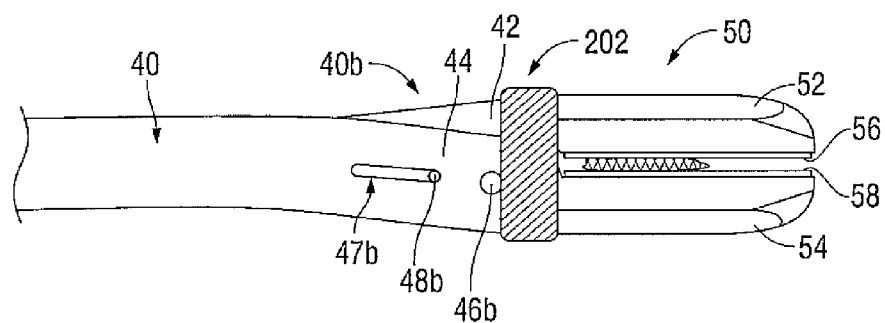
FIG. 6 is an enlarged side, elevational view of the vertically bifurcated shaft of FIG. 1A including an elastic band disposed about a distal portion of the bifurcated shaft and a portion of an end effector assembly thereof.

For example, as shown in FIG. 6, jaw compression pressure (and the maintenance of the shaft halves in the initial position) may be facilitated by a cowling 202 (e.g., an elastic band). Cowling 202 may surround at least a portion of end effector assembly 50 and/or the bifurcated shaft (e.g., shaft 40). More particularly, cowling 202 is disposed about pivot 46a (FIG. 1) and pivot 46b, coupling pivots 46a, 46b to one another to ensure adequate jaw compression pressure of jaw members 52 and 54 about tissue. Cowling 202 may be disposed within a notch or recess (not explicitly shown) defined within jaw members 52, 54 to retain cowling 202 in position relative to jaw members 52, 54 and/or to reduce the overall diameter of end effector assembly 50. Further, a biasing member, (e.g., a spring) (not shown) may be utilized to provide added jaw compression pressure to end effector assemblies 50, 150, in addition to, or in place of cowling 202.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a shaft having a proximal end and a bifurcated distal end defining a first shaft portion and a second shaft portion;
    an end effector assembly disposed at the distal end of the shaft, the end effector assembly having first and second jaw members, at least one of the jaw members moveable relative to the other between an open position and a closed position for grasping tissue therebetween, each of the jaw members defining an opposed jaw surface, each of the jaw members independently coupled to one of the first and second shaft portions;
    wherein, the first and second shaft portions are configured to flex relative to one another during movement of the jaw members to the closed position to grasp tissue therebetween such that the opposed jaw surfaces of the jaw members are disposed in substantially parallel orientation relative to one another when grasping tissue therebetween; and
    a cowling retained within a notch defined within at least one of the shaft or the jaw members, the cowling configured to limit flexing of the first and second shaft portions relative to one another.

2. The surgical instrument according to claim 1, wherein the opposed jaw surfaces define electrically conductive tissue sealing surfaces adapted to connect to a source of energy for sealing tissue grasped therebetween.

3. The surgical instrument according to claim 2, wherein the first and second shaft portions are configured to flex relative to one another to achieve a uniform gap distance between the jaw members during tissue sealing.

4. The surgical instrument according to claim 2, wherein the first and second shaft portions are configured to flex relative to one another to achieve a uniform closure pressure between the jaw members during tissue sealing.

5. The surgical instrument according to claim 4, wherein the closure pressure between the jaw members is in the range of about 3 kg/cm$^2$ to about 16 kg/cm$^2$ when grasping tissue therebetween.

6. The surgical instrument according to claim 1, wherein the shaft is bifurcated about a vertical axis thereof to define a first side shaft portion and a second side shaft portion.

7. The surgical instrument according to claim 1, wherein the shaft is bifurcated about a horizontal axis thereof to define an upper shaft portion and a lower shaft portion.

8. The surgical instrument according to claim 1, wherein each of the jaw members is independently coupled to one of the first and second shaft portions via a floating pivot.

9. A surgical instrument, comprising:
    a shaft having a proximal end and a bifurcated distal end defining a first shaft portion and a second shaft portion;
    an end effector assembly disposed at the distal end of the shaft, the end effector assembly having first and second jaw members, each jaw member defining an opposed jaw surface, the first jaw member coupled to the first shaft portion via a first floating pivot, the second jaw member coupled to the second shaft portion via a second floating pivot independent of the first floating pivot, the first and second jaw members rotatable about the first and second floating pivots, respectively, relative to one another between an open position and a closed position for grasping tissue therebetween, the first and second floating pivots moveable relative to one another as the jaw members are rotated to the closed position for grasping tissue therebetween such that the opposed jaw surfaces of the jaw members are disposed in substantially parallel orientation relative to one another when grasping tissue therebetween; and
    a cowling retained within a notch defined within at least one of the shaft or the jaw members, the cowling configured to limit flexing of the first and second shaft portions relative to one another.

10. The surgical instrument according to claim 9, wherein the first and second floating pivots are moveable relative to one another to achieve a uniform closure pressure between the jaw members when grasping tissue therebetween.

11. The surgical instrument according to claim 10, wherein the closure pressure between the jaw members is in the range of about 3 kg/cm$^2$ to about 16 kg/cm$^2$ during tissue sealing.

12. The surgical instrument according to claim 9, wherein the opposed jaw surfaces define electrically conductive tissue sealing surfaces adapted to connect to a source of energy for sealing tissue grasped therebetween.

13. The surgical instrument according to claim 12, wherein the first and second floating pivots are moveable relative to one another to achieve a uniform gap distance between the jaw members during tissue sealing.

14. The surgical instrument according to claim 9, wherein the shaft is bifurcated about a vertical axis thereof to define a first side shaft portion and a second side shaft portion.

15. The surgical instrument according to claim 9, wherein the shaft is bifurcated about a horizontal axis thereof to define an upper shaft portion and a lower shaft portion.

16. The surgical instrument according to claim 9, wherein the first and second shaft portions are configured to flex relative to one another to permit movement of the first and second floating pivots relative to one another.

* * * * *